United States Patent
Finkman et al.

(10) Patent No.: US 9,326,661 B2
(45) Date of Patent: May 3, 2016

(54) LINE OF SIGHT WIRELESS ENDOSCOPY (71) Applicant: GYRUS ACMI INC., Southborough, MA (US)

(72) Inventors: Shai Finkman, Haifa (IL); Adi Navve, Kfar-Saba (IL)

(73) Assignee: GYRUS ACMI, INC., Southborough, MA (US)

( * ) Notice: Subject to any disclaimer, the term of this patent is extended or adjusted under 35 U.S.C. 154(b) by 352 days.

(21) Appl. No.: 14/082,265

(22) Filed: Nov. 18, 2013

(65) Prior Publication Data

US 2015/0141751 A1    May 21, 2015

(51) Int. Cl.
*A61B 1/04* (2006.01)
*A61B 1/00* (2006.01)
*A61B 1/05* (2006.01)
*H04B 10/114* (2013.01)
(Continued)

(52) U.S. Cl.
CPC .......... *A61B 1/00013* (2013.01); *A61B 1/00045* (2013.01); *A61B 1/05* (2013.01); *H04B 10/114* (2013.01); *A61B 2017/00221* (2013.01); *H04B 10/116* (2013.01)

(58) Field of Classification Search
CPC .. A61B 1/00013; A61B 1/00045; A61B 1/05; A61B 1/00016; A61B 19/5202; A61B 2017/00221; H04B 10/114; H04B 10/1141; H04B 10/116; H04B 10/1149
See application file for complete search history.

(56) References Cited

U.S. PATENT DOCUMENTS 4,975,926 A * 12/1990 Knapp .................. H04B 1/707
                                                            375/141
5,278,536 A *  1/1994 Furtaw .................. H04B 3/542
                                                           340/12.32
5,354,993 A    10/1994 Kedmi et al.
(Continued)

FOREIGN PATENT DOCUMENTS

EP    2430972 A1    3/2012
EP    2579618 A1    4/2013
(Continued)

OTHER PUBLICATIONS

Minh et al, "Indoor Gigabit Optical Wireless Communications:Challenges and Possibilities", IEEE, ICTON , Th.A3.1, pp. 1-6, 2010.
(Continued)

*Primary Examiner* — John P Leubecker
(74) *Attorney, Agent, or Firm* — D. Kligler I.P. Services Ltd.

(57) ABSTRACT

Endoscope imaging apparatus, including an endoscope, which is configured to be inserted into a body cavity of a patient and an image sensor configured by means of the endoscope to form an image of the body cavity, and to transmit image signals in response to the image formed. The apparatus further includes an optical transmitter, physically connected to the endoscope, and configured to receive the image signals, to encode the image signals, and to transmit optical radiation comprising the encoded image signals. An optical receiver with a mounting fixture is configured for connection to a light boom, and is also configured to receive the optical radiation, to decode the optical radiation to recover the image signals, and to transmit the recovered image signals. A camera control unit is configured to receive the recovered image signals and in response to display the image on a screen.

19 Claims, 6 Drawing Sheets

(51) Int. Cl.
*H04B 10/116* (2013.01)
*A61B 17/00* (2006.01)

(56) References Cited

U.S. PATENT DOCUMENTS

| | | | |
|---|---|---|---|
| 5,986,787 A * | 11/1999 | Ohshima | H04B 10/40 398/127 |
| 6,101,038 A | 8/2000 | Herbert | |
| 6,718,005 B2 | 4/2004 | Hamada et al. | |
| 6,900,777 B1 * | 5/2005 | Hebert | A61B 19/52 345/30 |
| 2002/0022763 A1 * | 2/2002 | Sano | A61B 1/00016 600/109 |
| 2004/0156638 A1 | 8/2004 | Graves et al. | |
| 2007/0179342 A1 * | 8/2007 | Miller | A61B 1/267 600/188 |
| 2008/0139881 A1 * | 6/2008 | Cover | A61B 1/00016 600/103 |
| 2011/0004276 A1 | 1/2011 | Blair et al. | |
| 2011/0028790 A1 * | 2/2011 | Farr | A61B 1/00052 600/187 |
| 2011/0275894 A1 * | 11/2011 | Mackin | A61B 1/00016 600/109 |
| 2012/0035418 A1 * | 2/2012 | Talbert | A61B 1/00016 600/109 |
| 2012/0116155 A1 * | 5/2012 | Trusty | A61B 1/00013 600/109 |
| 2012/0200685 A1 | 8/2012 | Kawasaki et al. | |
| 2013/0012777 A1 * | 1/2013 | Baum | A61B 1/00013 600/110 |
| 2013/0088155 A1 | 4/2013 | Maxik et al. | |
| 2013/0184591 A1 | 7/2013 | Tesar | |
| 2014/0023984 A1 * | 1/2014 | Weatherly | A61B 1/00016 433/31 |
| 2014/0107416 A1 * | 4/2014 | Birnkrant | A61B 1/00016 600/110 |

FOREIGN PATENT DOCUMENTS

| | | |
|---|---|---|
| JP | 2010207459 A | 9/2010 |
| TW | 200927059 A | 7/2009 |
| WO | 02054959 A2 | 7/2002 |

OTHER PUBLICATIONS

Omega, ICT-213311, "Seventh Framework Programme Theme 3 Information & Communication Technologies (ICT)", pp. 1-58, Apr. 18, 2011.

International Application # PCT/US14/64708 Search Report dated Feb. 16, 2015.

* cited by examiner

LINE OF SIGHT WIRELESS ENDOSCOPY

FIELD OF THE INVENTION

The present invention relates generally to imaging, and specifically to imaging using an endoscope.

BACKGROUND OF THE INVENTION

U. S. Patent Application 2011/0004276, to Blair et al., whose disclosure is incorporated herein by reference, describes a system for detection of the presence or absence of objects in medical procedures via an interrogation and detection system which includes a controller and a plurality of antennas positioned along a patient support structure. The antennas may be attached to a lightshade.

U. S. Patent Application 2013/0184591, to Tesar, whose disclosure is incorporated herein by reference, describes an endoscope that is claimed to be useful for near infrared imaging, and that is stated to have transmitting members that transmit between about 95% and 99.9% of the energy at a wavelength within the infrared spectrum.

U. S. Patent Application 2004/0156638, to Graves et al., whose disclosure is incorporated herein by reference, describes an atmospheric optical data transmission system. The system has first and second transceivers spaced a substantial distance from each other and having telescopes aimed at each other.

Taiwan Patent Application TW 2009/27059, to Suen et al., describes an image acquisition processing system having an image-sensing unit, an image display unit, and an image database of medical treatment. The image-sensing unit includes an image sensor, an optical component, and an IC communication component.

Europe Patent Application EP 2430972 to Ogawa et al., describes a hand-held wireless endoscope. The endoscope is stated to have a first antenna and a second antenna. The application further states that an image obtained by imaging the inside of a body cavity is converted into a wireless signal, and transmission/reception of the wireless signal to/from the outside is enabled through the first and/or second antenna.

U. S. Patent Application 2012/0200685, to Kawaaki et al., whose disclosure is incorporated herein by reference, describes an endoscope scope having a generation unit that photographs a subject. The scope generates moving image data and still image data, and has a reception unit that receives a transmission instruction for the still image data, and a transmission unit that wirelessly transmits the still image data.

Japan Patent Application JP 2010/207459 to Kiyoshi et al., whose disclosure is incorporated herein by reference, describes wireless endoscope system. The system is stated to securely and easily start wireless communication between a desired processor close at hand and an endoscope system even if a plurality of endoscope systems of the same model exist around.

U.S. Pat. No. 5,354,993, to Kedmi et al., whose disclosure is incorporated herein by reference, describes an optical communication link for a medical imaging gantry having continuous line of sight communications between transmitters and receivers.

U.S. Pat. No. 6,718,005, to Hamada et al., whose disclosure is incorporated herein by reference, describes a noncontact type of signal transmission device that performs noncontact transmission of signals between a first member and a second member by using light.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides an endoscope imaging apparatus, including:

an endoscope, configured to be inserted into a body cavity of a patient;

an image sensor configured by means of the endoscope to form an image of the body cavity, and to transmit image signals in response to the image formed;

an optical transmitter, physically connected to the endoscope, configured to receive the image signals, to encode the image signals, and to transmit optical radiation comprising the encoded image signals;

an optical receiver with a mounting fixture configured for connection to a light boom, the receiver being configured to receive the optical radiation, to decode the optical radiation to recover the image signals, and to transmit the recovered image signals; and a camera control unit, configured to receive the recovered image signals and in response to display the image on a screen.

Typically the optical transmitter includes a single transmitter. The apparatus may include a reflector, and the optical radiation may be transmitted as specular radiation via the reflector. Alternatively, the apparatus may include a diffuser, and the optical radiation may be transmitted as diffuse radiation via the diffuser.

In a disclosed embodiment the apparatus includes a lamp attached to the light boom, and the mounting fixture is configured to connect the optical receiver to the light boom via the lamp.

In a further disclosed embodiment the optical receiver is configured to transmit the recovered image signals as a radio-frequency image signal. Alternatively or additionally, the optical receiver is configured to transmit the recovered image signals via a cable connected to the camera control unit.

The optical transmitter may consist of a first optical transmitter and a second optical transmitter respectively transmitting a first cone of the optical radiation and a second cone, different from the first cone, of the optical radiation. Typically, a controller is configured to detect that a first clear line of sight exists between the first optical transmitter and the optical receiver, and that a second clear line of sight does not exist between the second optical transmitter and the optical receiver. The controller may be configured to transmit a first control signal to the first optical transmitter so as to maintain the first transmitter transmitting the first cone of the optical radiation, and to transmit a second control signal to the second optical transmitter to power down the second optical transmitter.

In an alternative embodiment the apparatus includes a controller which is configured to provide radio-frequency control signals to the optical transmitter in response to the recovered image signals.

There is further provided, according to an embodiment of the present invention a method for imaging, including:

inserting an endoscope into a body cavity of a patient;

configuring, by means of the endoscope, an image sensor to form an image of the body cavity;

transmitting image signals in response to the image formed;

physically connecting an optical transmitter to the endoscope and configuring the optical transmitter to receive the image signals, to encode the image signals, and to transmit optical radiation comprising the encoded image signals;

providing an optical receiver with a mounting fixture configured for connection to a light boom;

configuring the receiver to receive the optical radiation, to decode the optical radiation to recover the image signals, and to transmit the recovered image signals; and receiving the recovered image signals and in response displaying the image on a screen.

The present invention will be more fully understood from the following detailed description of the embodiments thereof, taken together with the drawings in which:

DETAILED DESCRIPTION OF EMBODIMENTS

Overview

An embodiment of the present invention provides endoscope imaging apparatus. The apparatus consists of an endoscope that is configured to be inserted into a body cavity of a patient. The endoscope has an image sensor, which may be in a distal or proximal region of the endoscope, that forms an image of the body cavity, and that transmits image signals in response to the image formed. An optical radiation transmitter is physically connected to the endoscope, typically by being directly attached to the endoscope although in some embodiments the transmitter is connected to the endoscope by a cable. The transmitter receives the image signals, encodes the image signals, and then transmits optical radiation comprising the encoded image signals.

The apparatus further includes one or more optical receivers, having respective mounting fixtures for connection to a light boom. Typically, one or more of the receivers comprises a system controller for the imaging apparatus. The one or more optical receivers receive the optical radiation from the transmitter, decode the optical radiation to recover the image signals, and transmit the recovered image signals directly via a cable, or as radio-frequency signals to a camera control unit. The camera control unit receives the recovered image signals and in response displays the image acquired by the image sensor on a screen.

The imaging apparatus operates by transmitting optical radiation from the endoscope to optical receivers, and such transmission requires a clear line of sight between a transmitter and a receiver in order for the transmission to be successful. During a medical procedure that typically requires using a light boom, connecting the optical receivers to the light boom maximizes the probability of there being a clear line of sight between an optical radiation transmitter coupled to the endoscope and the receivers.

DETAILED DESCRIPTION

In the disclosure and in the claims, optical radiation is assumed to comprise electromagnetic radiation, in the visible or near-visible spectrum, that requires a clear line of sight between an optical radiation transmitter and an optical radiation receiver in order for there to be successful transmission therebetween. Also in the disclosure and in the claims, radio-frequency (RF) signals are assumed to comprise electromagnetic radiation that is not in the visible or near-visible spectrum, and that does not require a clear line of sight between an RF signal transmitter and an RF signal receiver in order for there to be successful transmission therebetween.

Figure 1:
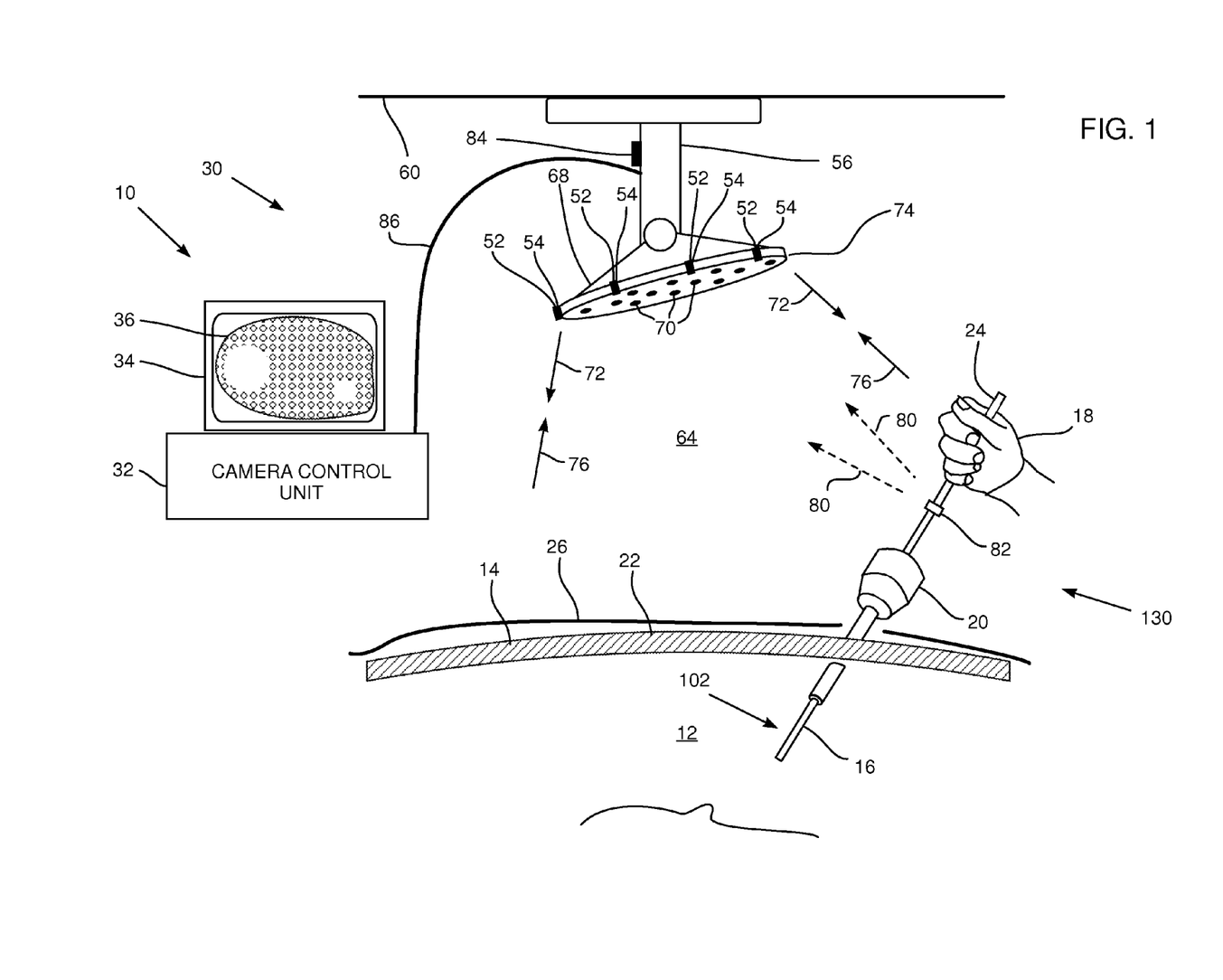
FIG. 1 is a schematic illustration of an endoscopic imaging system, according to an embodiment of the present invention.

Reference is now made to FIG. 1, which is a schematic illustration of an endoscopic imaging system 10, according to an embodiment of the present invention. System 10 may be used in an invasive medical procedure, typically a minimally invasive procedure, on a body cavity 12 of a human patient 14 in order to image part or all of the body cavity. By way of example, in the present description the body cavity is assumed to be the abdomen of patient 14, and body cavity 12 is also referred to herein as abdomen 12. However, it will be understood that system 10 may be used to image substantially any human body cavity, such as the bladder, the bronchium, or the chest, or a non-human cavity.

System 10 comprises an endoscope 16 which is inserted, during the procedure, by a medical professional 18 into abdomen 12 using a trocar 20 which penetrates abdomen wall 22. In order to perform the insertion, professional 18 typically holds the endoscope by a proximal end 24 of the endoscope. During the procedure the patient is typically at least partially covered by a sterile covering 26.

System 10 is operated by a system controller 30, and the software for controller 30 may be downloaded to the controller in electronic form, over a network, for example. Alternatively or additionally, the software may be provided on non-transitory tangible media, such as optical, magnetic, or electronic storage media.

A camera control unit (CCU) operates endoscope 16, and in addition drives a screen 34, upon which an image 36 acquired by the endoscope is presented. Image 36 is an image of a section of abdomen 12 viewed by the endoscope.

System 10 comprises one or more optical receivers 52 that are connected by respective mounting fixtures 54 to a light boom 56. The connection may be direct to the light boom, so that typically the receivers are an integral part of the boom, or indirect via other elements attached to the light boom. In the following description system controller 30 is assumed to be incorporated into one of receivers 52. However, there is no necessity that controller 30 is incorporated into a receiver, so that the controller may be a stand-alone unit, or may be incorporated into any other element of system 10. Light boom is typically fixedly attached to a ceiling 60 of an operating theater 64 wherein system 10 functions, although in some embodiments the light boom may be fixedly attached to a movable gantry within the operating theater. Light boom 56 holds a lamp 68 which may be oriented by professional 18, typically so that a plurality of lights 70 in the lamp project optical radiation into a range of projection directions 72 within theater 64. In a disclosed embodiment, illustrated and described in more detail with respect to FIG. 2, optical receivers 52 are attached by their fixtures 54 to a rim 74 of lamp 68.

Typically, fixtures 54 and receivers 52 are configured so that the receivers receive optical radiation from receiving directions 76 which have approximately the same orientation but opposite directions as range of projection directions 72.

In embodiments of the present invention, receivers 52 receive optical radiation 80 from redirecting optics 82 installed in endoscope 16. The production of optical radiation 80, and the operation of redirecting optics 82, are described in more detail with reference to FIG. 3.

Other elements of system 10, that are identified numerically in FIG. 1, are described below with reference to FIG. 2 and FIG. 3.

Figure 2:
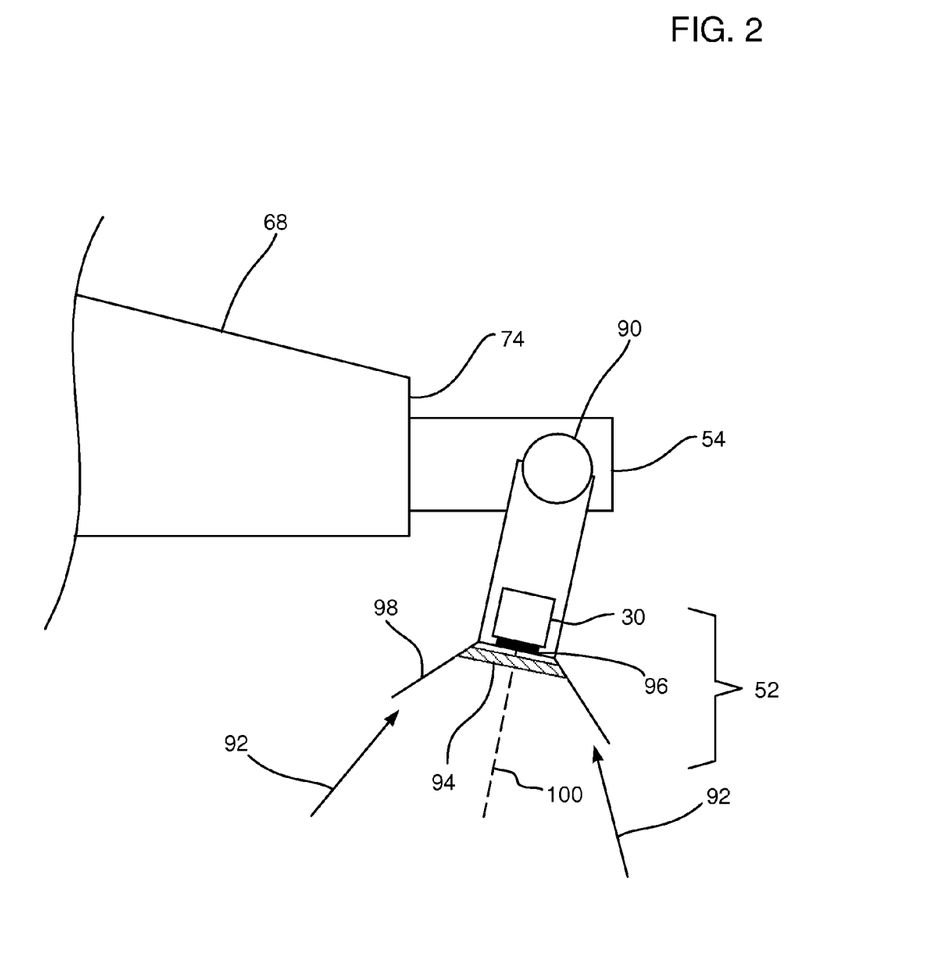
FIG. 2 is a schematic diagram illustrating the attachment of optical receivers, according to an embodiment of the present invention.

FIG. 2 is a schematic diagram illustrating the attachment of optical receivers 52 to rim 74, according to an embodiment of the present invention. As stated above, receivers 52 are connected, directly or indirectly, by respective fixtures 54 to light boom 56. In the embodiment illustrated in FIG. 2, the connection is indirect and is implemented by attaching the receivers to an intermediate element, comprising lamp 68, and by way of example fixtures 54 are assumed to be attached to the lamp at rim 74 of the lamp. Each fixture 54 may comprise a rotatable ball joint 90, which allows an operator of system 10 to adjust a range 92 of receiving directions within which each receiver 52 is operative in receiving optical radiation. Typically, although not necessarily, each range 92 is a subset of receiving directions 76.

Each receiver 52 comprises a respective optical detector 96, typically a photodiode, which is mounted within a respective housing 98. As illustrated in the diagram, at least one of receivers 52 may incorporate system controller 30. Housing 98 is typically in the form of a conical or paraboloidal mirror, which concentrates incoming optical radiation onto detector 96, and the dimensions of housing 98 may be adjusted to set the extent of range 92 for each receiver 92. Typically the extent of range 92 for all receivers is approximately the same, at approximately ±30° measured with respect to an axis of symmetry 100 of the receiver. However, in some embodiments, the extents are different, for example, some extents may be approximately ±20°, whereas other extents are approximately ±40°. Typically, a narrow-band filter 94 is placed in front of detector 96, the filter serving to restrict optical radiation received by detector 96 to a relatively narrow pass-band of optical wavelengths.

Figure 3:
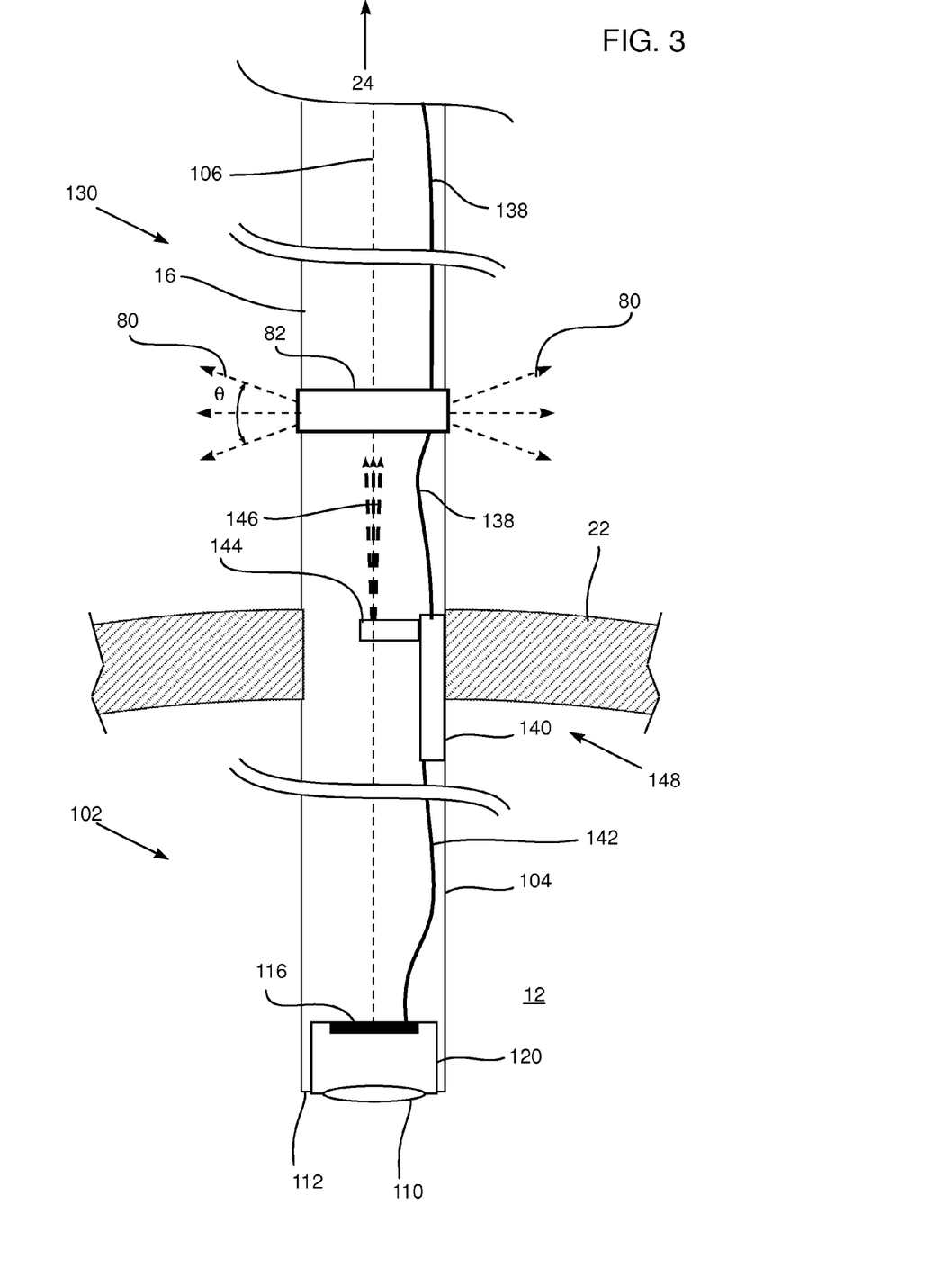
FIG. 3 is a schematic cross-sectional diagram of an endoscope, according to an embodiment of the present invention.

FIG. 3 is a schematic cross-sectional diagram of endoscope 16, according to an embodiment of the present invention. Endoscope 16 is shown after having penetrated abdomen wall 22, so that a distal end 102 of the endoscope is within abdomen 12. (For simplicity. trocar 20 is not shown in the diagram.) Endoscope 16 is formed as a tube 104, typically a cylindrical tube having an axis of symmetry 106, and focusing optical elements 110, which focus incoming radiation from a section of abdomen 12, are installed at a distal tip 112 of the tube. Elements 110 are configured so that the focused radiation from the elements forms an image of the abdomen section on an image sensor 116. In the present disclosure, by way of example, sensor 116 and optical elements 110 are assumed to be installed together in the endoscope as a camera 120.

However, there is no necessity that sensor 116 is located at the distal tip, so that in other embodiments of the present invention, sensor 116 is located in a proximal region 130, distant from distal end 102, of endoscope 16. In embodiments where the sensor is located in such a proximal region of the endoscope, the focused radiation from optic elements 110 may be conveyed to sensor 116 using relay optics and/or an optical fiber bundle. Those having ordinary skill in the art will be able to adapt the description, mutatis mutandis, for embodiments where sensor 116 is located in a proximal region of the endoscope.

Sensor circuitry 140 receives its operating power via a cable 138. The power may be provided by a battery installed in the endoscope or from a line supply. Sensor circuitry 140 is connected via a cable 142 to sensor 116, and the circuitry and the cable serve to provide power, driving, and control signals to sensor 116. In addition, image signals from sensor 116 are conveyed via cable 142 to circuitry 140, which processes the image signals, typically by amplification and filtration. Circuitry 140 also comprises an optical radiation generator 144, typically a LED (light emitting diode), or a VCSEL (vertical cavity surface emitting laser), the generator being configured to radiate optical radiation corresponding to the pass-band of filter 94. The wavelength of the radiation is typically, although not necessarily, outside the visible spectrum. For example, the radiation emitted by generator 144 may comprise infra-red (IR) radiation. Circuitry 140 encodes the processed image signals derived from sensor 116, and incorporates the encoded signals into the optical radiation transmitted by generator 144, by modulation of the optical radiation. Circuitry 140 and generator 144 thus act as an optical transmitter 148. The modulation of the optical radiation is typically amplitude and/or frequency modulation, although any other convenient form of modulation that is suitable for incorporating the information of the processed encoded image signals into the optical radiation may be used.

Generator 144 transmits its modulated optical radiation, as a relatively narrow cone of radiation 146, and the generator is configured to transmit the cone of radiation approximately along axis 106. Redirecting optics 82 are located in proximal region 130 of endoscope 16, in an area of the endoscope that is external to wall 22 of the patient, and that is distal with respect to proximal end 24. Redirecting optics 82 are configured to receive cone of radiation 146, and to redirect the received radiation as redirected radiation 80 so that the redirected radiation transmits in directions that are approximately orthogonal to axis 106, and are typically within range 92.

In some embodiment redirecting optics 82 are configured to specularly reflect cone of radiation 146. The redirected specular radiation is enclosed within an angle θ, and in one embodiment θ ranges between +30° and −30° with respect to a plane orthogonal to axis 106. However, in other embodiments extents of angle θ may have values other than +30° and −30°, and suitable ranges for angle θ may be determined by an operator of system 10 without undue experimentation. Typically, redirecting optics 82 are configured as a conical mirror, although other forms of optical elements, with the specular functionality for the redirecting optics described above, will be apparent to those having ordinary skill in the optical arts.

Alternatively, in some embodiments of the present invention, redirecting optics 82 are configured as a diffuser that diffuses incoming cone of radiation 146, and the redirected diffuse radiation from the optics may be transmitted into a solid angle of up to 4π steradians.

Returning to FIG. 1, each optical receiver 52 is configured to receive and decode redirected optical radiation from redirecting optics 82. The configuration of a given optical receiver is typically so that only if there is a direct line of sight between optics 82 and the given receiver is the receiver able to receive and process radiation 80. Such a configuration limits the power required to be transmitted by transmitter 148 in order for receivers 52 to be able to successfully receive and decode radiation 80. In one embodiment, the receivers 52 operate while lamps 70 are powered down, so as to minimize interference with the receivers. However, because of the presence of filter 94, it is not necessary for lamps 70 to be powered down in order for receivers 52 to function, and in other embodiments receivers 52 operate while the lamps are powered up.

Each optical receiver 52 decodes its received optical radiation to recover the image signals that have been encoded into the received radiation. The recovered image signals may typically be conveyed to CCU 32 via a cable 86 connecting the receiver to the CCU. In an alternative disclosed embodiment each optical receiver 52 is configured to transmit a generally omnidirectional radio-frequency (RF) image signal having the recovered image signals incorporated therein. Further alternatively, optical receivers 52 may be connected to a central RF transmitter 84, typically attached to light boom 56, which receives the recovered image signals from the receivers and which transmits the recovered image signals as a generally omnidirectional RF image signal. The frequency at which the RF signals are transmitted may be of the order of 1 GHz, in order to accommodate the relatively high data rate required for real-time transmission of the image signals. However, frequencies greater than or less than 1 GHz may also be used. In transmitting the RF image signals, any convenient protocol may be used.

CCU 32 is configured to receive the recovered image signals via cable 86, or via the RF signals from transmitter 84, or from receivers 52. CCU 32 processes the recovered image signals to present an image, corresponding to the image acquired by sensor 116, on screen 34. Typically, CCU 32 also analyzes the recovered image signals, and conveys its analysis to controller 30 via cable 86 or via the RF signals referred to above. The analysis typically includes image signal levels as well as noise levels. In response controller 30 formulates control values for elements in endoscope 16, and transmits these values as generally omnidirectional RF control signals, which are received by circuitry 140. Circuitry 140 decodes the RF control signals, and generates the control signals for sensor 116 referred to above, as well as control parameters for circuitry 140. The control signals for sensor 116 may include a desired frame rate and/or a desired resolution of each frame, and the control parameters for circuitry 140 may include a power level at which generator 144 is to operate so that image 36 presented on screen 34 has an acceptable signal to noise (S/N) ratio. Typically the RF control signals are transmitted with a protocol that has a low bandwidth, sufficient for the control data, but not suitable for the image signals. In some embodiments the RF control signals are transmitted using a BTLE (Bluetooth low energy) or an NFC (near field communication) protocol.

Figure 4:
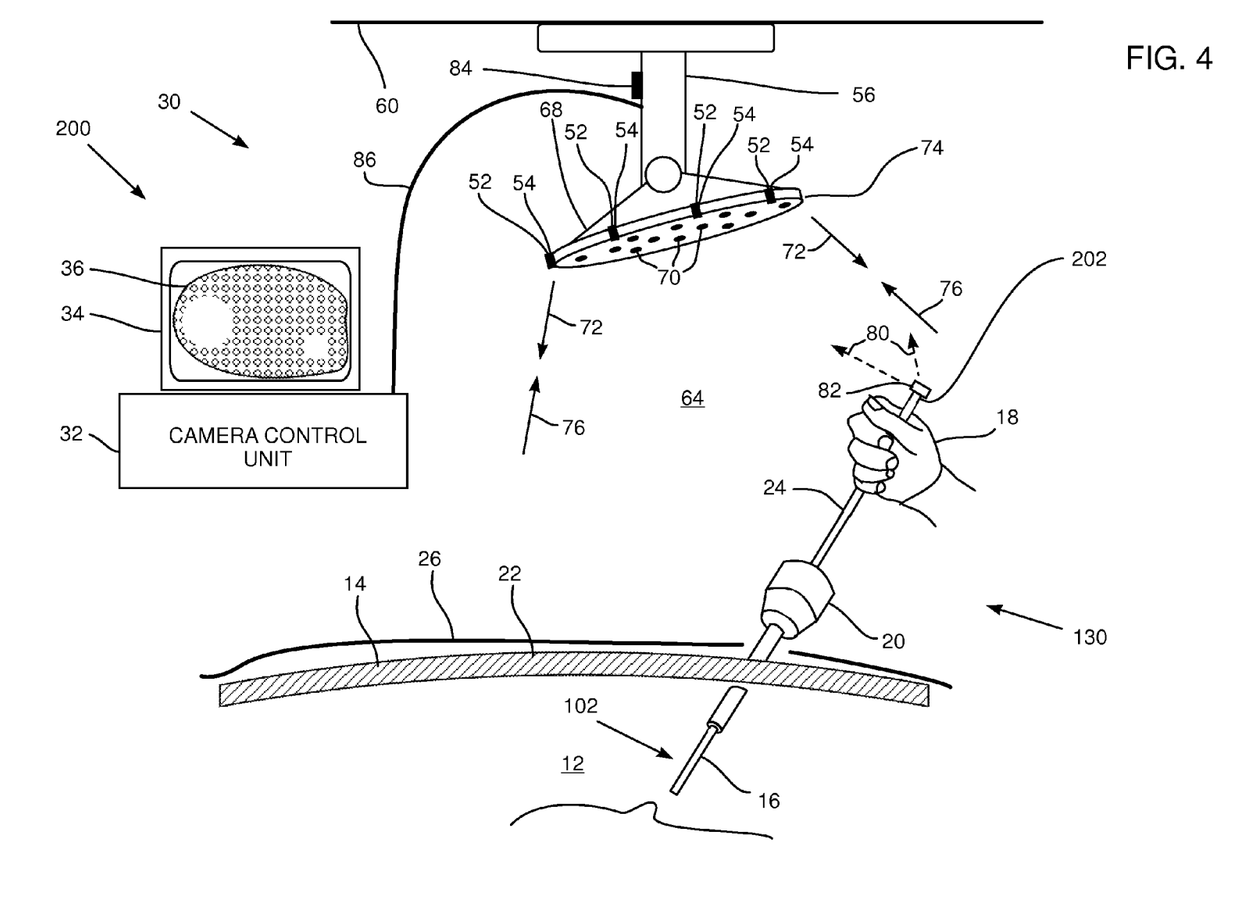
FIG. 4 is a schematic illustration of an endoscopic imaging system, according to an alternative embodiment of the present invention.

FIG. 4 is a schematic illustration of an endoscopic imaging system 200, according to an alternative embodiment of the present invention. Apart from the differences described below, the operation of system 200 is generally similar to that of system 10 (FIGS. 1, 2, and 3), and elements indicated by the same reference numerals in both systems 200 and 10 are generally similar in construction and in operation. In system 200, redirecting optics 82 are located proximally to their position in system 10, such as at a most proximal point 202 of proximal end 24. To accommodate the change of location of optics 82, circuitry 140 and/or generator 144 may need to be relocated, possibly to within proximal end 24. Alterations, mutatis mutandis, to the description herein to accommodate the change of location will be apparent to those having ordinary skill in the art.

Figure 5:
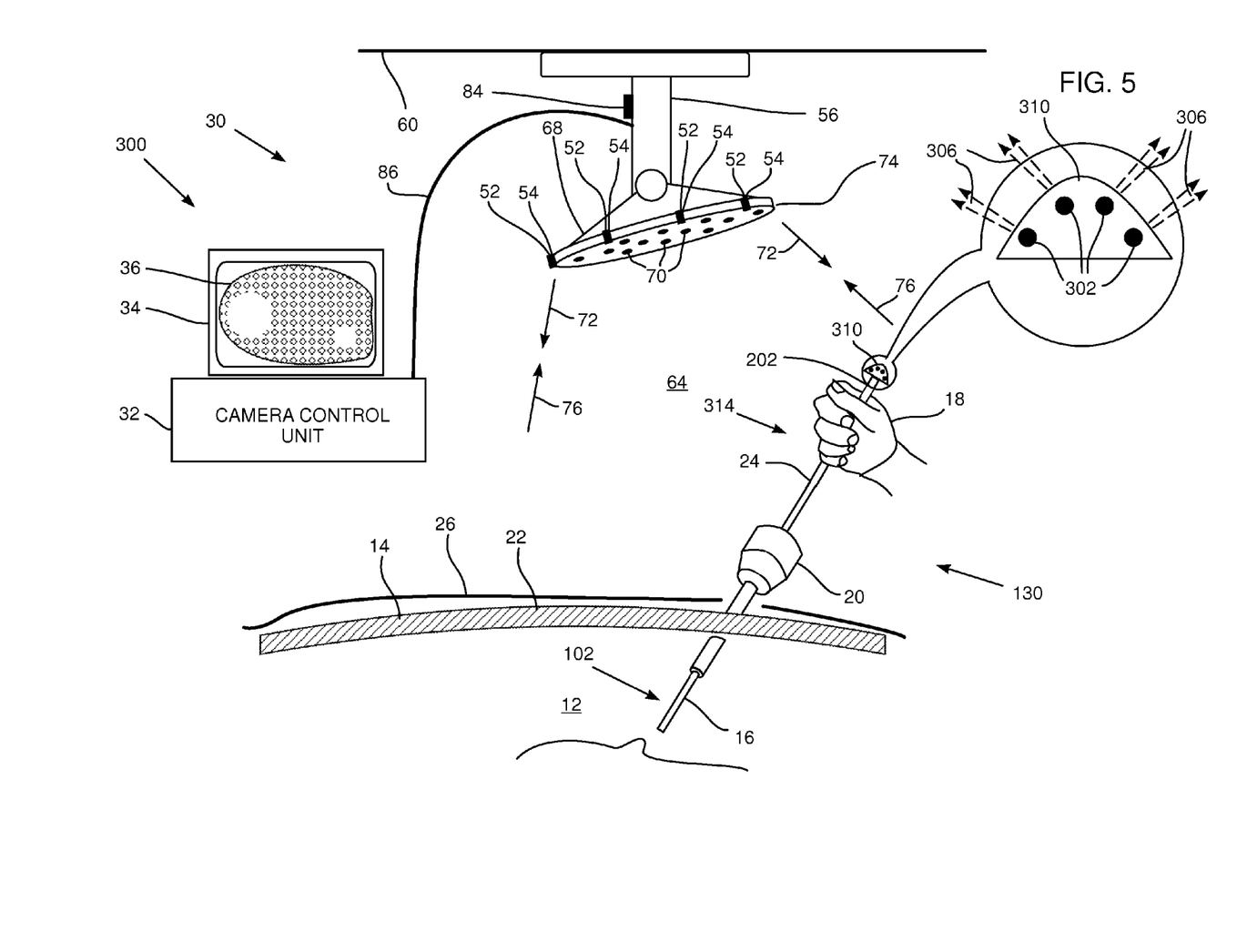
FIG. 5 is a schematic illustration of an endoscopic imaging system, according to a further alternative embodiment of the present invention.

FIG. 5 is a schematic illustration of an endoscopic imaging system 300, according to a further alternative embodiment of the present invention. Apart from the differences described below, the operation of system 300 is generally similar to that of systems 10 and 200 (FIGS. 1, 2, 3, and 4), and elements indicated by the same reference numerals in systems 300, 200, and 10 are generally similar in construction and in operation. In contrast to systems 10 and 200, there are no redirecting optics 82 used in system 300. In place of optics 82, system 300 uses a plurality of optical generators 302, each generally similar to generator 144 and having respective cones 306 of radiation. Optical generators 302 are grouped as a cluster 310 of radiators, and the cone of radiation of each generator 302 within the cluster is oriented to be different from the cones of the other generators. Typically the orientation of the cones is distributed approximately evenly over a solid angle of at least $2\pi$ steradians. Cluster 310 may be attached to any convenient proximal region of endoscope 16, outside patient 14. In one embodiment cluster 310 is installed at most proximal point 202 of proximal end 24.

While the wavelength of radiation transmitted by each generator 302 may typically be in a single band, the radiations of each generator 302 may be at a different specific wavelength, so that the generators may be identified by receivers 52. Alternatively or additionally, the identification may be by time and/or frequency keying of the radiations.

In one embodiment all generators 302 may be driven by a single circuit 314, substantially similar to circuitry 140. Additional electronic elements may be incorporated, as required, into circuitry 140 to form circuit 314, so as to enable the radiations of the different generators to be identified. Such additional elements will be apparent to those having ordinary skill in the art.

In an alternative embodiment, each generator 302 is driven by a respective circuit substantially similar to circuitry 140, each of the respective circuits being configured to enable the radiations of the different generators to be identified.

Except as otherwise indicated, in the following description generators 302 are assumed to be driven by single circuit 314.

Controller 30 may use the RF control signals referred to above to transmit a desired power level for each generator 302 to single circuit 314. For example, in an initial phase of operation of system 300, all generators 302 may transmit at full optical power, and controller 30 may identify which generators produce optical radiations that are received by receivers 52. Typically, controller 30 is configured to select as identified generators those whose cone of radiation 306 is towards receivers 52, and which have a direct line of sight to the receivers. The identification may be implemented by measuring the radiation power levels of the received radiation.

Once the identification has been performed, controller 30 may transmit RF control signals to circuit 314 to power down generators 302 whose radiations are not received by the receivers. The initial phase may be repeated, as necessary, to identify generators 302 to be powered on, or powered down. Such a process minimizes the power needed for generators 302 to provide acceptable image signals to receivers 52 while maintaining an acceptable S/N ratio. Alternatively, other methods for identifying generators 302 to be powered on, so as to provide acceptable image signals while maintaining an acceptable S/N ratio, may be implemented for system 300. Such methods will be apparent to those having ordinary skill in the art, and are assumed to be comprised within the scope of the present invention.

Figure 6:
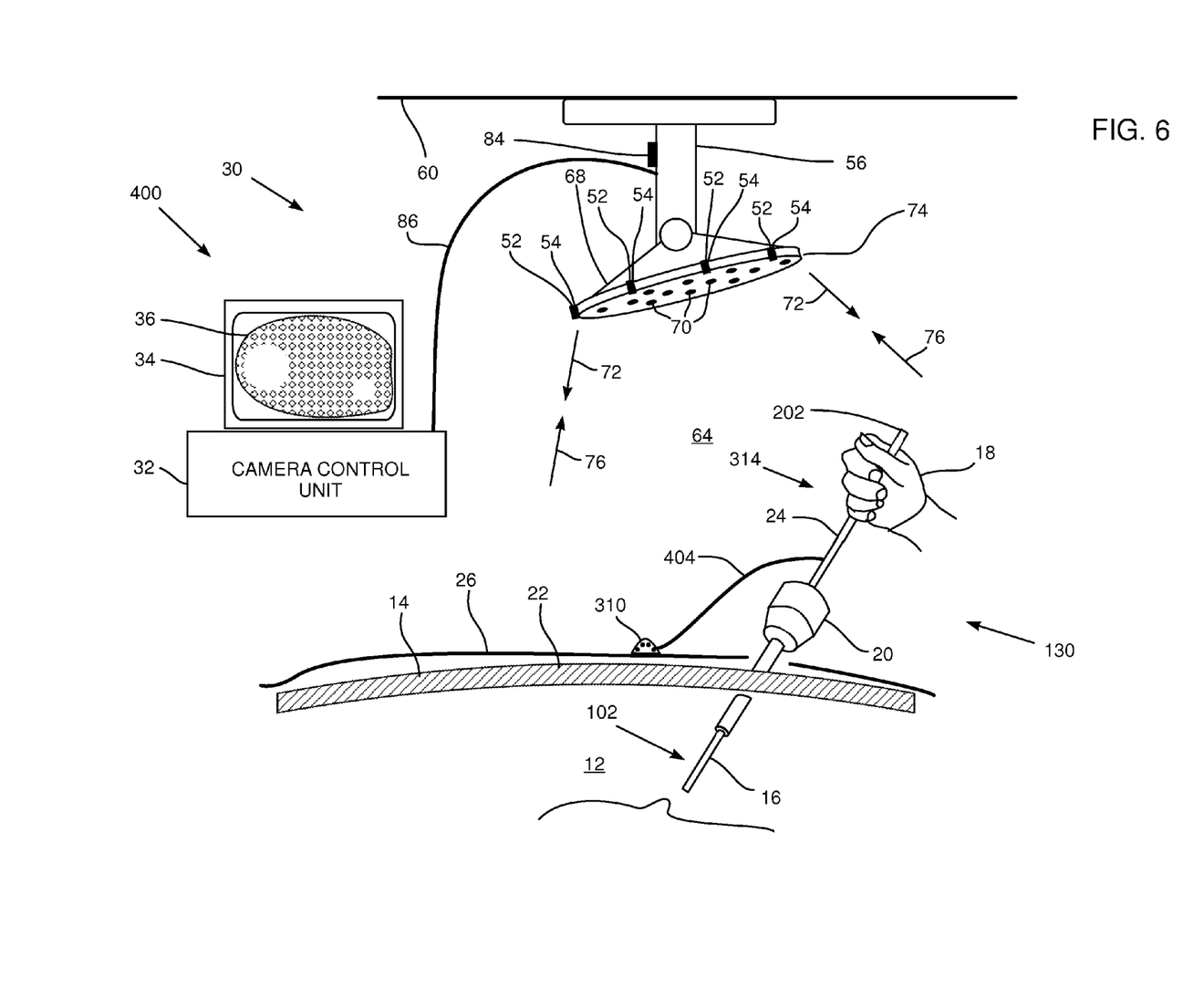
FIG. 6 is a schematic illustration of an endoscopic imaging system, according to a yet further alternative embodiment of the present invention.

FIG. 6 is a schematic illustration of an endoscopic imaging system 400, according to a yet further alternative embodiment of the present invention. Apart from the differences described below, the operation of system 400 is generally similar to that of system 300, and elements indicated by the same reference numerals in systems 300 and 400 are generally similar in construction and in operation. In contrast to system 300, wherein cluster 310 is attached to a region of endoscope 16, in system 400 cluster 310 is physically separated from the endoscope. In this case cluster 310 is connected by a cable 404 to endoscope 16, the cable serving to transfer power, control, and image signals to generators 302 in cluster 310 via circuit 314. Cluster 310 may be positioned in any convenient position, in theater 64, that has a clear line of sight to receivers 52. In one embodiment cluster 310 is placed on covering 26.

It will be appreciated that the embodiments described above are cited by way of example, and that the present invention is not limited to what has been particularly shown and described hereinabove. For example, system 300 and system 400 may be configured as a single system which is convertible, according to requirements of an operator of the system, between the configuration of system 300 and that of system 400. Thus, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Endoscope imaging apparatus, comprising:
    an endoscope, configured to be inserted into a body cavity of a patient;
    an image sensor configured by means of the endoscope to form an image of the body cavity, and to transmit image signals in response to the image formed;
    an optical transmitter, physically connected to the endoscope, configured to receive the image signals, to encode the image signals, and to transmit optical radiation comprising the encoded image signals;
    an optical receiver with a mounting fixture configured for connection to a light boom, the receiver being configured to receive the optical radiation, to decode the optical radiation to recover the image signals, and to transmit the recovered image signals as a radio-frequency image signal; and
    a camera control unit, configured to receive the recovered image signals and in response to display the image on a screen.

2. The apparatus according to claim 1, wherein the optical transmitter comprises a single transmitter.

3. The apparatus according to claim 2, and comprising a reflector, and wherein the optical radiation is transmitted as specular radiation via the reflector.

4. The apparatus according to claim 2, and comprising a diffuser, and wherein the optical radiation is transmitted as diffuse radiation via the diffuser.

5. The apparatus according to claim 1, and comprising a lamp attached to the light boom, and wherein the mounting fixture is configured to connect the optical receiver to the light boom via the lamp.

6. The apparatus according to claim 1, wherein the optical receiver is configured to transmit the recovered image signals via a cable connected to the camera control unit.

7. The apparatus according to claim 1, wherein the optical transmitter comprises a first optical transmitter and a second optical transmitter respectively transmitting a first cone of the optical radiation and a second cone, different from the first cone, of the optical radiation.

8. The apparatus according to claim 7, and comprising a controller which is configured to detect that a first clear line of sight exists between the first optical transmitter and the optical receiver, and that a second clear line of sight does not exist between the second optical transmitter and the optical receiver.

9. The apparatus according to claim 8, wherein the controller is configured to transmit a first control signal to the first optical transmitter so as to maintain the first transmitter transmitting the first cone of the optical radiation, and to transmit a second control signal to the second optical transmitter to power down the second optical transmitter.

10. Endoscope imaging apparatus, comprising:
    an endoscope, configured to be inserted into a body cavity of a patient;
    an image sensor configured by means of the endoscope to form an image of the body cavity, and to transmit image signals in response to the image formed;
    an optical transmitter, physically connected to the endoscope, configured to receive the image signals, to encode the image signals, and to transmit optical radiation comprising the encoded image signals;
    an optical receiver with a mounting fixture configured for connection to a light boom, the receiver being configured to receive the optical radiation, to decode the optical radiation to recover the image signals, and to transmit the recovered image signals;
    a camera control unit, configured to receive the recovered image signals and in response to display the image on a screen; and
    a controller which is configured to provide radio-frequency control signals to the optical transmitter in response to the recovered image signals.

11. A method for imaging, comprising:
    inserting an endoscope into a body cavity of a patient;
    configuring, by means of the endoscope, an image sensor to form an image of the body cavity;
    transmitting image signals in response to the image formed;
    physically connecting an optical transmitter to the endoscope and configuring the optical transmitter to receive the image signals, to encode the image signals, and to transmit optical radiation comprising the encoded image signals;
    providing an optical receiver with a mounting fixture configured for connection to a light boom;
    configuring the receiver to receive the optical radiation, to decode the optical radiation to recover the image signals, and to transmit the recovered image signals signals as a radio-frequency image signal; and
    receiving the recovered image signals and in response displaying the image on a screen.

12. The method according to claim 11, wherein the optical transmitter comprises a single transmitter.

13. The method according to claim 12, and comprising transmitting the optical radiation as specular radiation via a reflector.

14. The method according to claim 12, and comprising transmitting the optical radiation as diffuse radiation via a diffuser.

15. The method according to claim 11, and comprising attaching a lamp to the light boom, and configuring the mounting fixture to connect the optical receiver to the light boom via the lamp.

16. The method according to claim 11, wherein the optical transmitter comprises a first optical transmitter and a second optical transmitter respectively transmitting a first cone of the optical radiation and a second cone, different from the first cone, of the optical radiation.

17. The method according to claim 16, and comprising detecting that a first clear line of sight exists between the first optical transmitter and the optical receiver, and that a second clear line of sight does not exist between the second optical transmitter and the optical receiver.

18. The method according to claim 17, and comprising transmitting a first control signal to the first optical transmitter so as to maintain the first transmitter transmitting the first cone of the optical radiation, and transmitting a second control signal to the second optical transmitter to power down the second optical transmitter.

19. The method according to claim 11, and comprising providing radio-frequency control signals to the optical transmitter in response to the recovered image signals.

\* \* \* \* \*